United States Patent [19]

Descamps et al.

[11] 4,012,394
[45] Mar. 15, 1977

[54] INDOLE DERIVATIVES

[75] Inventors: Marcel Descamps, Crainhem; Henri Inion, Wemmel, both of Belgium

[73] Assignee: Labaz, Paris, France

[22] Filed: Aug. 4, 1975

[21] Appl. No.: 601,919

Related U.S. Application Data

[62] Division of Ser. No. 438,214, Jan. 31, 1974, Pat. No. 3,946,029.

[30] Foreign Application Priority Data

Feb. 16, 1973 United Kingdom ............ 07866/73

[52] U.S. Cl. ............ 260/293.61; 260/247.5 FP; 260/296 B; 424/248.57; 424/263; 424/267; 424/248.58
[51] Int. Cl.² .................. C07D 401/06
[58] Field of Search ... 260/293.61, 296 B, 247.5 FP; 424/248, 263, 267; 438/214

[56] References Cited

UNITED STATES PATENTS 2,814,625  11/1957  Speeter ........................ 260/296
3,686,213  8/1972   Poletto et al. ............... 260/326.15

Primary Examiner—G. Thomas Todd
Attorney, Agent, or Firm—Mason, Kolehmainen, Rathburn & Wyss

[57] ABSTRACT

3-Indolyl pyridyl ketones of the general formula:

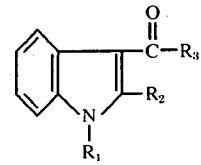

and pharmaceutically acceptable acid addition salts thereof wherein
$R_1$ represents
a straight- or branched-chain saturated or unsaturated alkyl group having not more than 6 carbon atoms, a benzyl group optionally substituted in the aromatic portion by a chlorine atom or a methoxy group
or

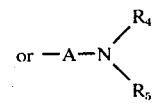

wherein
A represents an alkylene chain of from 2 to 6 carbon atoms and $R_4$ and $R_5$, which may be the same or different, are each an alkyl group having from 1 to 5 carbon atoms, or $R_4$ and $R_5$ are joined together to form with the nitrogen atom a piperidino, pyrrolidino or morpholino group,
$R_2$ represents
a branched-or straight-chain alkyl group having from 1 to 4 carbon atoms, a phenyl group optionally substituted by a fluorine, chlorine, or bromine atom or a methoxy or cyclohexyl group; and
$R_3$ represents
a 2-pyridyl, 3-pyridyl or 4-pyridyl group.

They are effective as fibrinolytic and anti-inflammatory agents.

3 Claims, No Drawings

INDOLE DERIVATIVES

This is a division of application Ser. No. 438,214, filed Jan. 31, 1974, now U.S. Pat. No. 3,946,029.

This invention relates to novel indole derivatives having pharmacological activity, to pharmaceutical and veterinary compositions containing them and to a method of preparing the said derivatives.

The indole derivatives with which the invention is concerned are represented by the general formula:

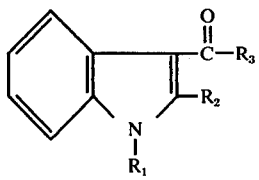

I wherein

R₁ represents
a straight- or branched-chain saturated or unsaturated alkyl group having not more than 6 carbon atoms, a benzyl group optionally substituted in the aromatic portion by a chlorine atom or a methoxy group
or

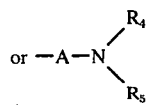

wherein
A represents an alkylene chain of from 2 to 6 carbon atoms and R₄ and R₅, which may be the same or different, are each an alkyl group having from 1 to 5 carbon atoms, or
R₄ and R₅ are joined together to form with the nitrogen atom a piperidino, pyrrolidino or morpholino group,
R₂ represents
a brahched-or straight-chain alkyl group having from 1 to 4 carbon atoms, a phenyl group optionally substituted by a fluorine, chlorine, or bromine atom or a methoxy or cyclohexyl group ; and
R₃ represents
a 2-pyridyl, 3-pyridyl or 4-pyridyl group.

The pharmaceutically acceptable acid addition salts of the compounds of formula I are also included within the scope of the invention.

As demonstrated further on, it has been found that the compounds of the invention possess marked fibrinolytic activity and some of them a pronounced anti-inflammatory effect also.

Another object of the invention is therefore a method of inducing fibrinolysis or treating inflammation in a mammal by administering to said mammal at least one indole as defined hereabove.

The compounds of formula I may be prepared by condensing in an inert organic medium, for example dimethylformamide, hexamethylphosphoramide or toluene, an indole derivative of the general formula:

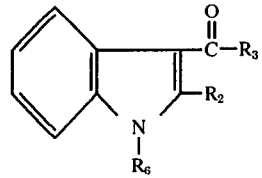

II wherein R₂ and R₃ have the same meanings as in formula I and R₆ represents an alkali metal, preferably sodium or potassium, with a halogenated compound of the general formula:

$$R_1 - X$$

III wherein R₁ has the same meaning as in formula I and X represents a chlorine, bromine or iodine atom, to form the required indole derivative of formula I which, if desired, may be reacted with an organic or inorganic acid to provide a pharmaceutically acceptable acid addition salt.

The compounds of formula II may be obtained by reacting an indole derivative of the formula:

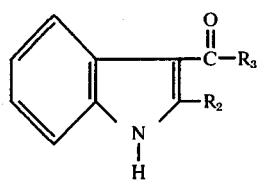

IV wherein R₂ and R₃ have the same meanings as in formula I, with an alkali metal amide or hydride, the alkali metal preferably being sodium or potassium.

The compounds of formula IV are either known compounds having been described in British Patent No. 1,318,300, or may be prepared from the corresponding 2-substituted-indoles by the method described in the said British Patent.

The indole derivatives of the invention have been found to possess useful pharmacological properties in the animal body and in particular marked fibrinolytic activity. Certain compounds of the invention also possess a pronounced anti-inflammatory activity.

The fibrinolytic activity is likely to render these compounds valuable in the treatment of thrombo-embolic states. For the treatment of these conditions the technique at present employed is based upon anti-coagulants. This type of medication, although satisfactory to a certain degree, is not without danger. When writing of the treatment of cardio-vascular diseases, C. RABY in his book "Biologie des Hemorragies et des Thromboses" (Masson & Cie, 1966) emphasises this point. On the subject of anti-coagulants, he says : "When they are given in insufficient doses, they are without effect and protection is purely illusory. When they are given to excess they become dangerous and cause haemorrhagic complications which are sometimes fatal. When they are ill-chosen, they may be both useless and harmful." Further on, this same author recommends that in order to combat incipient or existing states of thrombosis, the most logical therapy would be to employ substances which are directly thrombolytic. It may thus be reasonably concluded that the search for an agent capable of combating thrombo-embolic states through the medium of fibrinolytic action is a matter of primary importance.

In this connection, it may be added that the fibrinolytic compounds of the invention exert a direct dissolving effect upon thrombi at the level of the vascular wall.

Compounds of a chemical structure similar to that of the compounds represented by formula I above, namely indoles having a pyridylcarbonyl group in the 3-position and possessing fibrinolytic properties, are already known, having been published in British Pat. No. 1,318,300.

It has now been found, in accordance with the present invention, that it is possible to increase to a considerable degree the fibrinolytic activity of the 2-substituted (3-indolyl) pyridyl ketones described in British Pat. No. 1,318,300, by replacing the hydrogen of the indolic nitrogen with a $R_1$ group as defined with reference to the above formula I. It has been observed that the substitution of these 3-indolyl pyridyl ketones in the 1-position of the indolyl group renders the compounds so substituted as much as 15 times more fibrinolytic than the corresponding indoles which bear no substituent in the 1-position.

This unexpected and quite inexplicable discovery has made it possible to prepare a number of fibrinolytic compounds as defined by formula I above, which compounds constitute a valuable source of potentially powerful substances for the treatment of thrombo-embolic syndromes. Examples of such compounds are (1-methyl-2-isopropyl-3-indolyl) (4-pyridyl) ketone (1-γ-piperidinopropyl-2-isopropyl-3-indolyl) (2-pyridyl) ketone, and [1-β-dimethylaminoethyl-2-4-methoxyphenyl)-3-indolyl] (3-pyridyl) ketone as well as their pharmaceutically acceptable acid addition salts.

Certain compounds of the invention have been found to possess an anti-inflammatory activity which is much more intense than that of acetylsalicylic acid although inferior to that of indomethacin, one of the most potent anti-inflammatory agents known up to present. However, these compounds of the invention are considerably less toxic and have a much weaker ulcer-producing action than indomethacin. It may thus be possible, with the compounds of the invention, to increase the dosage of the active compound without any accompanying increase in irritant action or toxicity. As regards anti-inflammatory activity, the preferred compound of the invention is (1-methyl-2-isopropyl-3-indolyl) (3-pyridly) ketone.

Pharmacological trials have been carried out with a view to determining the fibrinolytic activity of the compounds of the invention. The procedure followed was that of TODD (J. Pathol. Bacter. 78, 281, 1959) adapted to the vena cave inferior of the rat as described in Arzn. Forschumg, 20, 358, 1970.

In these trials, there was used one single dose of 10 mg/kg. of each compound in admixture with diluent or excipient, the dose being administered intraperitoneally.

Male rats weighing 150 to 200 g. and having fasted for 24 hours were divided into two groups. The animals of one group were given the above-indicated dose of the compound to be tested. The animals of the other group, which constituted the control group, were treated in exactly the same way as the test animals except that the active compound present in the dose administered to the test animals was replaced by an equivalent quantity of the diluent or excipient used in the dose. After 40 minutes, the treated animals were sacrificed simultaneously with the control animals, the veins immediately removed, rinsed with physiological salt solution, frozen and cut into pieces having a thickness of 20 microns. On each piece, a film of fibrin was formed by the application of a bovine fibrinogenous solution, rich in plasminogen, and of a thrombin solution.

The preparations were all incubated at 37° C. for 30 minutes, which preliminary trials had shown to be the most suitable incubation period. All the preparations were then fixed with a 10% solution of neutral formol, stained with haematoxylin of Harris and covered with gelatine. Microscopic examination revealed three degrees of reaction namely:

Value = 0: The film of fibrin was intact.
Value = 1: The lysis zones in the endothelium were disseminated.
Value = 2: The lysis zones were larger and more or less joined.
Value = 3: The fibrin in contact with the endothelium was almost completely decomposed.

The fibrinolytic index represents the average of the values of the reactions obtained for each incubation.

The following Table expresses in percent the average increase in fibrinolytic effect obtained with the compounds tested as compared with the results observed with the control animals.

| $R_1$ | $R_2$ | $R_3$ | Fibrinolytic index in % |
|---|---|---|---|
| methyl | isopropyl | 2-pyridyl | +105 |
| β-dimethylaminoethyl | isopropyl | 2-pyridyl | +21 |
| γ-piperidinopropyl | isopropyl | 2-pyridyl | +123 |
| β-piperidinoethyl | isopropyl | 3-pyridyl | +77 |
| n-propyl | isopropyl | 3-pyridyl | +25 |
| β-dimethyaminoethyl | isopropyl | 3-pyridyl | +24 |
| γ-piperidinopropyl | isopropyl | 3-pyridyl | +18 |
| methyl | isopropyl | 4-pyridyl | +165 |
| β-dimethylaminoethyl | isopropyl | 4-pryidyl | +44 |
| γ-dimethylaminopropyl | isopropyl | 4-pyridyl | +30 |
| β-dimethylaminoethyl | n-propyl | 2-pyridyl | +50 |
| γ-dimethylaminopropyl | n-propyl | 2-pyridil | +66 |
| β-dimethylaminoethyl | 4-chloro-phenyl | 3-pyridyl | +40 |
| β-dimethylaminoethyl | 4-chloro-phenyl | 4-pyridyl | +42 |
| β-piperidinoethyl | 4-chloro-phenyl | 4-pyridyl | +50 |
| β-dimethylaminoethyl | 4-fluoro-phenyl | 4-pyridyl | +50 |
| β-dimethylaminoethyl | 4-fluoro-phenyl | 3-pyridyl | +90 |
| γ-dimethylaminopropyl | 4-fluoro-phenyl | 3-pyridyl | +75 |
| γ-dimethylaminopropyl | phenyl | 2-pyridyl | +46 |
| γ-dimethylaminopropyl | phenyl | 3-pyridyl | +46 |
| β-dimethylaminoethyl | phenyl | 2-pyridyl | +50 |
| β-dimethylaminoethyl | phenyl | 3-pyridyl | +96 |
| β-dimethylaminoethyl | 4-methoxy-phenyl | 2-pyridyl | +45 |
| β-dimethylaminoethyl | 4-methoxy-phenyl | 3-pyridyl | +133 |
| β-dimethylaminoethyl | 4-methoxy-phenyl | 4-pyridyl | +42 |

The same test was performed with the two compounds (2-isopropyl-3-indolyl) (3-and 4-pyridyl) ketones at a dosage of 10mg/kg and fibrinolytic indices of +5% and +10% respectively were obtained. Similary a test undertaken with 100 mg/kg of (2-n-propyl-3-indolyl)(2-pyridyl) ketone and (2-phenyl-3-indolyl)(3-pyridyl) ketone revealed fibrinolytic indices of + 2% and + 20% respectively.

Comparison of these results with those obtained with the corresponding N-substituted derivatives indicated in the above Table would suggest that the N-substituents employed play a useful role in intensifying the fibrinolytic effect.

The anti-inflammatory activity of the compounds of the invention was determined on the rat by means of the JANSSEN test involving the use of carragheenin as inflammatory agent.

Into the plantar aponeurosis of the back paws of a group of female rats 0.05 ml. of a 1% suspension of carragheenin was injected one hour after the compound to be tested had been administered by oral route. The size of the paw was measured by plethysmograph both before and three hours after administration of the carragheenin. The anti-inflammatory activity was calculated as the percentage of reduction of the resulting oedema as compared with control animals which had received the same dose of carragheenin without any anti-inflammatory agent. The $AD_{50}$ was taken as the amount of compound required to ensure a 50% reduction of the oedema.

Trials carried out with (1-methyl-2-isopropyl-3-indolyl) (3-pyridyl) ketone (hereinafter referred to as Compound A) in comparison with indomethacin, phenylbutazone and acetylsalicylic acid gave the following results:

| Compound | $AD_{50}$ (mg/kg) |
|---|---|
| Compound A | 15 |
| Indomethacin | 4 |
| Phenylbutazone | 22 |
| Acetylsalicylic acid | 110 |

These figures show that indomethacin is a more powerful anti-inflammatory agent than Compound A and that phenylbutazone and acetylsalicylic acid are less active than Compound A.

However, it has been found that Compound A is less toxic than both indomethacin and phenylbutazone. For example, the $LD_{50}$ of indomethacin was found to be 22.5 mg/kg. in rats by intragastric route and that of phenylbutazone 750 mg/kg. As against these figures, it was found that the $LD_{50}$ of Compound A, in the same condition, was 2,400 mg/kg.

This means that Compound A can be administered in higher doses and over longer periods than either indomethacin or phenylbutazone without undesirable side-effects.

As another means of evaluating the utility of the compounds of the invention as anti-inflammatory agents in comparison with the three substances indicated above, trials were carried out on fasting rats in order to determine the degree to which the compounds studied produced gastric ulcers in the animals so treated. These trials showed that indomethacin, as an ulcer-producing substance, was sixty times more irritant than Compound A, while phenylbutazone and acetylsalicylic acid were respectively twice and one-and-a-half times as irritant as Compound A. An index was also calculated by comparing the mean ulcer-producing dose expressed in mg/kg. with the $AD_{50}$ in mg/kg. found in the JANSSEN test.

The index figures obtained for Compound A as well as for indomethacin, phenylbutazone and acetylsalicylic acid are given hereunder:

| Compound | Index |
|---|---|
| Compound A | 20 |
| Indomethacin | 1.3 |
| Phenylbutazone | 7 |
| Acetylsalicylic acid | 2 |

These figures show that the irritant dose is much farther removed from the anti-inflammatory dose in the case of Compound A than in the case of indomethacin, phenylbutazone or acetylsalicylic acid.

A certain number of toxicity tests were also carried out on rats and mice and in particular acute toxicity tests.

In the rat, it was found that the $LD_{50}$ of Compound A administered by intraperitoneal route was 425 mg/kg. while the $LD_{50}$ in the mouse was 3,250 mg/kg. and 900 mg/kg. by intraperitoneal and intragastric routes respectively. These results were obtained after seven days of observation. Since the normal active pharmacological dose is in the region of 15 mg/kg., it is seen that the toxic doses are far in excess of this amount which means that there is a very wide margin of safety.

Other toxicity tests undertaken with (1-γ-dimethylaminopropyl-2-isopropyl-3-indolyl) (3-pyridyl) ketone show a $LD_{50}$ superior to 2,000 mg/kg. by intragastric route in the rat.

It will appreciated that for therapeutic use the compounds of the invention will normally be administered in the form of a pharmaceutical or veterinary composition comprising as an essential active ingredient at least one compound of Formulz I or a pharmaceutically acceptable acid addition salt thereof, in association with a pharmaceutical carrier therefor. The carrier may be a solid or liquid diluent or excipient of the kind normally employed in the production of medicaments ready for use, for example, distilled water, sodium chloride, lactose, talc, magnesium stearate, microcrystalline cellulose, colloidal silica, alginic acid, gelatine, polyvinylpyrrolidone, polyoxyethyleneglycol stearate, propyleneglycol, isopropyl palmitate or sodium carboxymethyl-cellulose. The composition may be made up in a form suitable for the desired mode of administration which may be by the oral, rectal or parenteral route, or by topical administration.

Advantageously for clinical use, the composition is made up in a dosage unit form adapted for the desired mode of administration. The dosage unit may be, for example a tablet, pill, packaged powder, capsule or suppository, or a discrete quantity of a syrup, cream, ointment, suspension or solution. The amount of active ingredient in each dosage unit will be such that one or more units are required for each therapeutic administration.

The following Examples illustrate the invention.

EXAMPLE 1

Preparation of (1-methyl-2-isopropyl-3-indolyl) (3-pyridyl) ketone

In a flask fitted with a mechanical stirrer, a vertical condenser, a dropping-funnel and a thermometer, were introduced 25 ml. of dimethylfornamide and 1.44 g. of a 50% suspension of sodium hydride in mineral oil. To this mixture was added drop-by-drop and at a temperature of 35° C. a solution of 5.2 g. of (2-isopropyl-3-indolyl) (3-pyridyl) ketone in 35 ml. of dimethylformamide. The reaction medium was stirred at 35° C. for one hour to complete the formation of the sodium derivative of (2-isopropyl-3-indolyl) (3-pyridyl) ketone and then 4.25 g. of methyl iodide were added drop-by-drop. The stirring was continued for 20 hours at a temperature of 40° C. after which the reaction medium was poured into water. The resulting mixture was extracted with dichlorethane, the solvent was evaporated off and the residue was recrystallised from heptane.

In this manner, 1.7 g. of (1-methyl-2-isopropyl-3-indolyl) (3-pyridyl) ketone was obtained, melting at 114° C., which represents a yield of 30.9 %. By following the same method as that described above but using the appropriate starting products, the compounds listed hereunder were prepared.

| Compound | Melting Point ° C |
|---|---|
| (1,2-dimethyl-3-indolyl) (3-pyridyl) ketone | 90 |
| (1-ethyl-2-methyl-3-indolyl) (3-pyridyl) ketone | 98 |
| (1-methyl-2-isopropyl-3-indolyl) (2-pyridyl) ketone | 75 |
| (1-methyl-2-isopropyl-3-indolyl) (4-pyridyl) ketone | 106 |
| (1-ethyl-2-isopropyl-3-indolyl) (3-pyridyl) ketone | 80 |
| (1-ethyl-2-isopropyl-3-indolyl) (2-pyridyl) ketone | 125 |
| (1-ethyl-2-isopropyl-3-indolyl) (4-pyridyl) ketone | 98 |
| (1-n-propyl-2-isopropyl-3-indolyl) (3-pyridyl) ketone | 94 |
| (1-n-butyl-2-isopropyl-3-indolyl) (3-pyridyl) ketone | 63 |
| (1-n-hexyl-2-isopropyl-3-indolyl) (3-pyridyl) ketone | B.P. 190 – 195 (0.01 mm/Hg) $n_D$ 20 = 1.5997 |
| (1-methyl-2-n-propyl-3-indolyl) (2-pyridyl) ketone hydrochloride | 130 |
| (1-methyl-2-n-propyl-3-indolyl) (4-pyridyl) ketone | 104 |
| (1-methyl-2-ethyl-3-indolyl) (3-pyridyl) ketone | 87 |
| (1-methyl-2-n-propyl-3-indolyl) (3-pyridyl) ketone | 104 |
| (1-methyl-2-isobutyl-3-indolyl) (3-pyridyl) ketone | 111 – 112 |
| (1-methyl-2-isobutyl-3-indolyl) (2-pyridyl) ketone | 67 |
| (1-methyl-2-isobutyl-3-indolyl) (4-pyridyl) ketone | 123 |
| (1-methyl-2-cyclohexyl-3-indolyl) (4-pyridyl) ketone | 148 |

EXAMPLE 2

Preparation of (1-methyl-2-n-butyl-3-indolyl) (3-pyridyl) ketone

In a flask fitted with a mechanical stirrer, a vertical condenser, a dropping-funnel and a thermometer were introduced 40 ml. of dry toluene and 2.7 g. of a 50% suspension of sodium amide in toluene. To this mixture was added drop-by-drop a solution of 6.5 g. of (2-n-butyl-3-indolyl) (3-pyridyl) ketone in 40 ml. of dry toluene and 20 ml. of dimethylformamide. The reaction medium was heated to 100° C. and this temperature was maintained until no more ammonia was given off. The mixture was cooled to 0° C. and then 4.9 g. of methyl iodide were added drop-by-drop to the reaction medium. This mixture was brought up to room temperature and stirring was maintained for 20 hours. The reaction medium was then poured into water and extracted with dichlorethane. The solvent was evaporated off and the residue obtained was recrystallised from heptane.

In this manner, 4,8g. of (1-methyl-2-n-butyl-3-indolyl) (3-pyridyl) ketone were obtained, melting at 89°–90° C. which represents a yield of 71.6%.

EXAMPLE 3

Preparation of (1-γ-piperidinopropyl-2-isopropyl-3-indolyl)(3-pyridyl) ketone oxalate In a flask fitted with a mechanical stirrer, a vertical condenser, a dropping-funnel and a thermometer were introduced 25 ml. of dimethylformamide and 1.25 g. of a 50% suspension of sodium hydride in mineral oil. To this mixture was added drop-by-drop and at a temperature of 35° C. a solution of 6.6 g. of (2-isopropyl-3-indolyl)(3-pyridyl) ketone in 35 ml. of dimethylformamide. The reaction medium was stirred for one hour at 35° C. to complete the formation of the sodium derivative of (2-isopropyl-3-indolyl)(3-pyridyl) ketone and then 4.8 g. of 1-piperidino-3-chloro-propane were added drop-by-drop. Stirring was maintained for 15 hours at a temperature of 40° C.; the reaction mixture was poured into water. The mixture was acidified with a diluted hydrochloric acid solution and extracted with dichlorethane. The aqueous phase was made alkaline and extracted with dichlorethane. The orgnic fractions were collected and then the solvent and the volatile fractions were evaporated under high vacuum. The residual oil was taken up in ether and the required oxalate was precipitated by adding an ethereal solution of oxalic acid. The precipitate was filtered off and recrystallised from absolute ethanol. In this manner, 8.4 g. of (1-γ-piperidinopropyl-2-isopropyl-3-indolyl) (3-pyridyl) ketone oxalate was obtained, melting at 218° C., which represents a yield of 70.5 %.

By following the same method as that described above but using the appropriate starting-products, the compounds listed hereunder were prepared:

| Compound | Melting Point° C |
|---|---|
| (1-β-dimethylaminoethyl-2-isopropyl-3-indolyl) (4-pyridyl) ketone dioxalate | 176 |
| (1-β-dimethylaminoethyl-2-isopropyl-3-indolyl) (3-pyridyl) ketone oxalate | 220 |
| (1-β-piperidinoethyl-2-isopropyl 3-indolyl) (3-pyridyl) ketone oxalate | 252 |
| (1-β-morpholinoethyl-2-isopropyl-3-indolyl) (3-pyridyl) ketone oxalate | 250 |
| (1-γ-dimethylaminopropyl-2-isopropyl-3-indolyl) (3-pyridyl) ketone sesquioxalate | 180 |
| (1-γ-dimethylaminopropyl-2-isopropyl-3-indolyl) (4-pyridyl) ketone oxalate | 232 |
| (1-γ-dimethylaminopropyl-2-isopropyl-3-indolyl) (2-pyridyl) ketone oxalate | 200 |
| (1-β-dimethylaminoethyl-2-isopropyl-3-indolyl) (2-pyridyl) ketone oxalate | 230 |
| (1-γ-piperidinopropyl-2-isopropyl-3-indolyl) (2-pyridyl) ketone oxalate | 215 |
| (1-γ-dimethylaminopropyl-2-n-propyl-3-indolyl) (2-pyridyl) ketone oxalate | 170 |
| (1-β-dimethylaminoethyl-2-n-propyl- | |

-continued

| Compound | Melting Point° C |
|---|---|
| 3-indolyl) (2-pyridyl) ketone oxalate | 202 |
| (1-β-dimethylaminoethyl-2-phenyl-3-indolyl) (2-pyridyl) ketone oxalate | 156 |
| (1-γ-dimethylaminopropyl-2-phenyl-3-indolyl) (2-pyridyl) ketone | 88 |
| (1-β-dimethylaminoethyl-2-phenyl-3-indolyl) (3-pyridyl) ketone oxalate | 232 |
| (1-γ-dimethylaminopropyl-2-phenyl-3-indolyl) (3-pyridyl) ketone sesquioxalate | 188 |
| (1-β-dimethylaminoethyl-2-phenyl-3-indolyl) (4-pyridyl) ketone sesquioxalate | 222 |
| (1-γ-dimethylaminopropyl-2-phenyl-3-indolyl) (4-pyridyl) ketone sesquioxalate | 198 |
| [1-β-dimethylaminoethyl-2-(4-fluoro-phenyl)-3-indolyl] (2-pyridyl) ketone oxalate | 188 |
| [1-γ-dimethylaminopropyl-2-(4-fluoro-phenyl)-3-indolyl] (2-pyridyl) ketone oxalate | 142 |
| [1-β-dimethylaminoethyl-2-(4-fluoro-phenyl)-3-indolyl] (3-pyridyl) ketone sesquioxalate | 160 |
| [1-γ-dimethylaminopropyl-2-(4-fluoro-phenyl)-3-indolyl] (3-pyridyl) ketone sesquioxalate | 176 |
| [1-β-dimethylaminoethyl-2-(4-fluoro-phenyl)-3-indolyl] (4-pyridyl) ketone sesquioxalate | 230 |
| [1-γ-dimethylaminopropyl-2-(4-fluoro-phenyl)-3-indolyl] (4-pyridyl) ketone sesquioxalate | 212 |
| [1-β-dimethylaminoethyl-2-(4-chloro-phenyl)-3-indolyl] (2-pyridyl) ketone sesquioxalate | 175 |
| [1-γ-dimethylaminopropyl-2-(4-chloro-phenyl)-3-indolyl] (2-pyridyl) ketone sesquioxalate | 135 |
| [1-β-dimethylaminoethyl-2-(4-chloro-phenyl)-3-indolyl] (3-pyridyl) ketone | 135 |
| [1-γ-dimethylaminopropyl-2-(4-chloro-phenyl)-3-indolyl] (3-pyridyl) ketone | 132 |
| [1-β-dimethylaminoethyl-2-(4-chloro-phenyl)-3-indolyl] (4-pyridyl) ketone dioxalate | 220 |
| [1-γ-dimethylaminopropyl-2-(4-chloro-phenyl)-3-indolyl] (4-pyridyl) ketone oxalate | 206 |
| [1-β-piperidinoethyl-2-(4-chloro-phenyl)-3-indolyl] (4-pyridyl) ketone | 161 |
| [1-γ-piperidinopropyl-2-(4-chloro-phenyl)-3-indolyl] (4-pyridyl) ketone sesquioxalate | 218 |
| [1-β-dimethylaminoethyl-2-(4-methoxy-phenyl)-3-indolyl] (2-pyridyl) ketone sesquioxalate | 164 |
| [1-γ-dimethylaminopropyl-2-(4-methoxy-phenyl)-3-indolyl] (2-pyridyl) ketone oxalate | 135 |
| [1-β-dimethylaminoethyl-2-(4-methoxy-phenyl)-3-indolyl] (3-pyridyl) ketone dioxalate | 206 |
| [1-γ-dimethylaminopropyl-2-(4-methoxy-phenyl)-3-indolyl] (3-pyridyl) ketone dioxalate | 188 |
| [1-β-dimethylaminoethyl-2-(4-methoxy-phenyl)-3-indolyl] (4-pyridyl) ketone oxalate | 190 |
| [1-γ-dimethylaminopropyl-2-(4-methoxy-phenyl)-3-indolyl] (4-pyridyl) ketone oxalate | 244 |
| [1-β-dimethylaminoethyl-2-(2-methoxy-phenyl)-3-indolyl] (4-pyridyl) ketone dioxalate | 210 |
| [1-γ-dimethylaminopropyl-2-(2-methoxy-phenyl)-3-indolyl] (4-pyridyl) ketone sesquioxalate | 207 |
| [1-β-dimethylaminoethyl-2-(4-bromo-phenyl)-3-indolyl] (3-pyridyl) ketone dioxalate | 203 |
| [1-γ-dimethylaminopropyl-2-(4-bromo-phenyl)-3-indolyl] (3-pyridyl) ketone dioxalate | 190 |
| [1-β-dimethylaminoethyl-2-(4-bromo-phenyl)-3-indolyl] (4-pyridyl) ketone dioxalate | 218 |
| [1-β-dimethylaminoethyl-2-(2-methoxy-phenyl)-3-indolyl] (2-pyridyl) ketone oxalate | 216 |
| [1-γ-dimethylaminopropyl-2-(2-methoxy-phenyl)-3-indolyl] (2-pyridyl) ketone oxalate | 210 |
| [1-β-dimethylaminoethyl-2-(2-methoxy-phenyl)-3-indolyl] (3-pyridyl) ketone | |
| [1-γ-dimethylaminopropyl-2-(2-methoxy-phenyl)-3-indolyl] (3-pyridyl) ketone | |
| [1-β-dimethylaminoethyl-2-(3-methoxy-phenyl)-3-indolyl] (3-pyridyl) ketone dioxalate | 205 |
| [1-γ-dimethylaminopropyl-2-(3-methoxy-phenyl)-3-indolyl] (3-pyridyl) ketone dioxalate | 214 |
| [1-β-dimethylaminoethyl-2-(3-methoxy-phenyl)-3-indolyl] (4-pyridyl) ketone dioxalate | 209 |
| [1-γ-dimethylaminopropyl-2-(3-methoxy-phenyl)-3-indolyl] (4-pyridyl) ketone dioxalate | 132 |
| [1-β-dimethylaminoethyl-2-(3-methoxy-phenyl)-3-indolyl] (2-pyridyl) ketone | |
| [1-γ-dimethylaminopropyl-2-(3-methoxy-phenyl)-3-indolyl] (2-pyridyl) ketone | |
| [1-β-dimethylaminoethyl-2-(2-chloro-phenyl)-3-indolyl] (2-pyridyl) ketone | |
| [1-β-dimethylaminoethyl-2-(2-chloro-phenyl)-3-indolyl] (3-pyridyl) ketone oxalate | 169 – 171 |
| [1-β-dimethylaminoethyl-2-(2-chloro-phenyl)-3-indolyl] (4-pyridyl) ketone | |
| [1-β-dimethylaminoethyl-2-(3-chloro-phenyl)-3-indolyl] (2-pyridyl) ketone | |

-continued

| Compound | Melting Point° C |
|---|---|
| [1-β-dimethylaminoethyl-2-(3-chloro-phenyl)-3-indolyl] (3-pyridyl) ketone | |
| [1-β-dimethylaminoethyl-2-(3-chloro-phenyl)-3-indolyl] (4-pyridyl) ketone | |
| [1-γ-dimethylaminopropyl-2-(4-bromo-phenyl)-3-indolyl] (4-pyridyl) ketone | |
| [1-β-dimethylaminoethyl-2-(4-bromo-phenyl)-3-indolyl] (2-pyridyl) ketone oxalate | 214 |
| [1-γ-dimethylaminopropyl-2-(4-bromo-phenyl)-3-indolyl] (2-pyridyl) ketone | |
| (1-β-pyrrolidinoethyl-2-isopropyl-3-indolyl) (3-pyridyl) ketone oxalate | 248 |
| (1-β-pyrrolidinoethyl-2-isopropyl-3-indolyl) (2-pyridyl) ketone sesquioxalate | 155 |

EXAMPLE 4

Preparation of
[1-(4-methoxy-benzyl)-2-isopropyl-3-indolyl] (3-pyridyl) ketone

In a flask, fitted with a mechanical stirrer, a vertical condenser, a dropping-funnel and a thermometer were introduced 25 ml. of dimethylformamide and 1.44 g. of a 50% suspension of sodium hydride in mineral oil. To this mixture was added drop-by-drop at a temperature of 35° C. a solution of 5.2 g. of (2-isopropyl-3-indolyl) (3-pyridyl) ketone in 35 ml. of dimethylformamide. The reaction medium was stirred for one hour at 35° C. to complete the formation of the sodium derivative of (2-isopropyl-3-indolyl) (3-pyridyl) ketone after which 4.7 g. of p-methoxy-benzyl chloride were added drop-by-drop. Stirring was maintained for 15 hours at a temperature of 40° C., and the mixture was then poured into water and extracted with dichlorethane. The solvent was evaporated off and the residue was recrystallised from heptane.

In this manner, 0.8 g. of [1-(4-methoxy-benzyl)-2-isopropyl-3-indolyl](3-pyridyl) ketone, melting at 190° C., was obtained, which represents a yield of 10.5 %.

By following the same method as that described above but using the appropriate starting-products, the compounds listed hereunder were prepared:

| Compound | Melting Point ° C. |
|---|---|
| (1-benzyl-2-isopropyl-3-indolyl) (3-pyridyl) ketone | 128 |
| [1-(4-chloro-benzyl-2-isopropyl-3-indolyl] (3-pyridyl) ketone | 134 |
| [1-(2-chloro-benzyl)-2-isopropyl-3-indolyl] (3-pyridyl) ketone | 129 |
| [1-(2-methoxy-benzyl)-2-isopropyl-3-indolyl] (3-pyridyl) ketone | 120 |

EXAMPLE 5

Preparation of
(1-allyl-2-isopropyl-3-indolyl)(4-pyridyl) ketone

In a flask fitted with a mechanical stirrer and a thermometer were introduced 30 ml. of hexamethylphosphoramide and 10.6 g. (0.04 mole) of (2-isopropyl-3-indolyl)(4-pyridyl) ketone.

The reaction medium was stirred until the ketone had completely dissolved and was then cooled to 0° C.

At this temperature 2.1 g. (0.044 mole) of a 50% suspension of sodium hydride in mineral oil was added. Stirring was maintained over 5 hours at room temperature to complete the formation of the sodium derivative of (2-isopropyl-3-indolyl)(4-pyridyl) ketone. The mixture was cooled to 0° C. and 4.8 g. (0.044 mole of allyl bromide were quickly added. The resulting mixture was brought up to room temperature and stirring was maintained for 20 hours, after which it was poured into water and extracted with dichlorethane. The solvent was evaporated off and the residue distilled under vacuum.

In this manner, 9.3 g. of (1-allyl-2-isopropyl-3-indolyl) (4-pyridyl) ketone were obtained, boiling at 165°–175° C. under 0.001 mm/Hg, which represents a yield of 76%.

By following the same method as that described above but using the appropriate starting-products, the compounds listed hereunder were prepared:

| Compound | |
|---|---|
| (1-allyl-2-isopropyl-3-indolyl) (2-pyridyl) ketone | B.P. 180–190° C (0.005 mm/Hg) |
| (1-allyl-2-isopropyl-3-indolyl) (3-pyridyl) ketone picrate | M.P. 174° C. |

EXAMPLE 6

Tablets were prepared by compressing ungranulated powders of the following ingredients in accordance with known pharmaceutical techniques:

| Ingredient | mg |
|---|---|
| (1-methyl-2-isopropyl-3-indolyl) (3-pyridyl) ketone | 100 |
| Lactose | 142 |
| Microcrystalline cellulose | 48 |
| Colloidal silica | 1 |
| Alginic acid | 6 |
| Magnesium stearate | 3 |
| | 300 |

EXAMPLE 7

Hard-gelatin capsules containing the following ingredients were prepared in accordance with known pharmaceutical techniques:

| Ingredient | mg |
|---|---|
| (1-methyl-2-isopropyl-3-indolyl) (3-pyridyl) ketone | 100 |
| Lactose | 100 |
| Colloidal silica | 5 |

| Ingredient | mg |
|---|---|
| | 205 |

We claim:

1. An indole derivative represented by the formula:

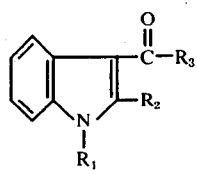

and pharmaceutically acceptable acid addition salts thereof, wherein

R₁ represents

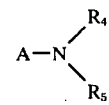

wherein
A represents an alkylene chain of from 2 to 6 carbon atoms and $R_4$ and $R_5$, which may be the same or different,
are each an alkyl group having from 1 to 5 carbon atoms, or $R_4$ and $R_5$ are joined together to form with the nitrogen atom a piperidino, pyrrolidino or morpholino group, $R_2$ represents
a branched-or straight-chain alkyl group having from 1 to 4 carbon atoms, a phenyl group optionally substituted by a fluorine, chlorine, or bromine atom, or a methoxy or cyclohexyl group; and $R_3$ represents a 2-pyridyl, 3-pyridyl or 4-pyridyl group.

2. (1-γ-piperidinopropyl-2-isopropyl-3-indolyl)(2-pyridyl) ketone and pharmaceutically acceptable acid addition salts thereof.

3. [1-β-dimethylaminoethyl-2-(4-methoxy-phenyl)-3-indolyl](3-pyridyl) ketone and pharmaceutically acceptable acid addition salts thereof.

* * * * *